United States Patent [19]

Mark et al.

[11] 4,324,261
[45] Apr. 13, 1982

[54] REFLEX HAMMER

[76] Inventors: Vernon H. Mark, 333 Leest, Brookline; Thomas D. Sabin, 28 Collins Rd., Newton, both of Mass.

[21] Appl. No.: 136,793

[22] Filed: Apr. 3, 1980

Related U.S. Application Data

[63] Continuation of Ser. No. 909,354, May 25, 1978, abandoned.

[51] Int. Cl.³ ............................................. A61B 5/10
[52] U.S. Cl. ....................................... 128/740; 128/54
[58] Field of Search ..................... 128/740, 744, 54; 145/61 D

[56] References Cited

U.S. PATENT DOCUMENTS

| | | | |
|---|---|---|---|
| 58,041 | 12/1911 | Wismer | 145/61 D |
| 703,790 | 7/1902 | Humiston | 145/29 R |
| 1,267,554 | 5/1918 | Karatsu | 128/740 |
| 1,478,388 | 12/1923 | Gray | 128/54 |
| 1,625,977 | 4/1927 | Bevier | 128/54 |
| 1,649,089 | 11/1927 | Volckening | 128/54 |
| 2,315,160 | 3/1943 | Newstedt et al. | 128/740 X |
| 2,330,882 | 10/1943 | Gray | 128/740 |
| 2,809,684 | 10/1957 | Lyon | 145/61 D |
| 2,858,898 | 11/1958 | Cinquini | 128/740 X |
| 3,344,781 | 10/1967 | Allen | 128/740 X |
| 3,515,125 | 6/1970 | Ruskin | 128/740 |
| 3,673,621 | 7/1972 | Pecorella | 7/143 |
| 4,154,273 | 5/1979 | Pollak | 145/29 R |

FOREIGN PATENT DOCUMENTS

| | | | |
|---|---|---|---|
| 2709340 | 9/1977 | Fed. Rep. of Germany | 128/740 |
| 296837 | 9/1928 | United Kingdom | 128/54 |
| 514663 | 11/1939 | United Kingdom | 128/54 |

Primary Examiner—Dalton L. Truluck
Attorney, Agent, or Firm—Wolf, Greenfield & Sacks

[57] ABSTRACT

A hammer having a head and flexible shaft for testing neurological reflexes. The head is formed with a striking edge and point opposite to it lying in a plane with the plane passing through the axis of the shaft at an acute angle. An annular tubular compressible resilient member forms a peripheral rim and defines the striking edge and point of the hammer head.

16 Claims, 6 Drawing Figures

REFLEX HAMMER

PRIOR APPLICATION

This application is a continuation of Application Ser. No. 909,354 filed May 25, 1978 and now abandoned.

BACKGROUND OF THE INVENTION

Reflex hammers which have heretofore been in common use have had a variety of functional limitations. For example, a common hatchet-type reflex hammer is made with a hatchet-like head connected to a rigid shaft. This type of reflex hammer, as well as others having rigid shafts, do not permit a full reflex response when used. These hammers have damping effects on the reflex. Other reflex hammers such as the "Queen Square" provide a head which is generally circular in configuration with the plane of the circle perpendicular to a long rigid handle. In addition to the limitations of the conventional hatchet reflex hammer, the Queen Square hammer cannot be stored easily and is also unwieldly in use. It is difficult in using the Queen Square hammer to always properly address the surface from which a reflex is to be elicited. Some of these defects and limitations are described in U.S. Pat. No. 3,515,125 which issued on June 2, 1970. That patent also discloses a reflex hammer in which the head can be adjusted to one of two positions in which the major plane of the head lies either in the plane perpendicular or parallel to the shaft. This patent, however, also has inherent limitations since neither of the two positions of the head relative to the shaft taught by that patent are ideal for eliciting reflexes from various parts of the body with either an edge or a pointed impacting head. Other attempts to provide an ideal reflex hammer that have appeared in patent literature but have not been completely satisfactory include U.S. Pat. No. 2,330,882 which issued on Oct. 5, 1963.

SUMMARY OF THE INVENTION

The present invention is intended to provide a reflex hammer which avoids the limitations referred to above and further provide a hammer which is ideal for all normal neurological reflex testing. In the present invention the head of the hammer is formed with an arcuate edge and pointed edge lying in a common plane with this plane lying in an acute angle to the axis of the shaft which is connected to the head. The shaft comprises a resilient member connecting a handle and the head. A tubular compressible rim defines the striking edge and forms the periphery of the head.

The angle between the flexible shaft and the plane in which the edge and point of the head lie allows the head of the hammer to be more easily lined up with the particular location from which a reflex is to be elicited. In use the hammer may be held in a variety of ways without any significant problems, while still allowing the surface which is to be impacted to be viewed during impact.

The specific shape of the hammer head permits a choice of point or striking surface depending upon the anatomical configuration of the reflex eliciting surface. Thus, for example, an elongated striking edge is provided by a slightly arcuate edge that extends generally lengthwise of the shaft. On the same head there is provided a dull point-like portion which can also be used for more localized impact. The head with an arcuate impacting edge and a point is shaped and positioned to allow the head to be attached at an acute angle to the shaft in such a manner as to allow both the edge and the pointed portion of the head to be addressed quite readily to any portion of the human body.

The flexible shaft which interconnects the handle and head eliminates the normal damping effect of reflex hammers incorporating rigid shafts. It has been found the amount of resilience that can be measured on a portion of the body is reduced with the time period in which the head is in contact with the eliciting surface. Thus, by providing a flexible shaft connecting the head to the handle the time during which the head is in contact with the reflexing surface is minimized.

The present invention also provides a head connected to a handle by a flexible shaft having sufficient resilience and flexibility as to increase the loading or spring effect of the head as it hits the impacting surface. In the present invention the arc of movement of the handle is less than that of the head during normal impact, as a result of the interconnection of the handle with the head by a flexible shaft.

DETAILED DESCRIPTION OF THE DRAWINGS

The foregoing objects and advantages of the present invention will be more clearly understood when considered in conjunction with the accompanying drawings, in which.

DESCRIPTION OF THE PREFERRED EMBODIMENT

Figure 1:
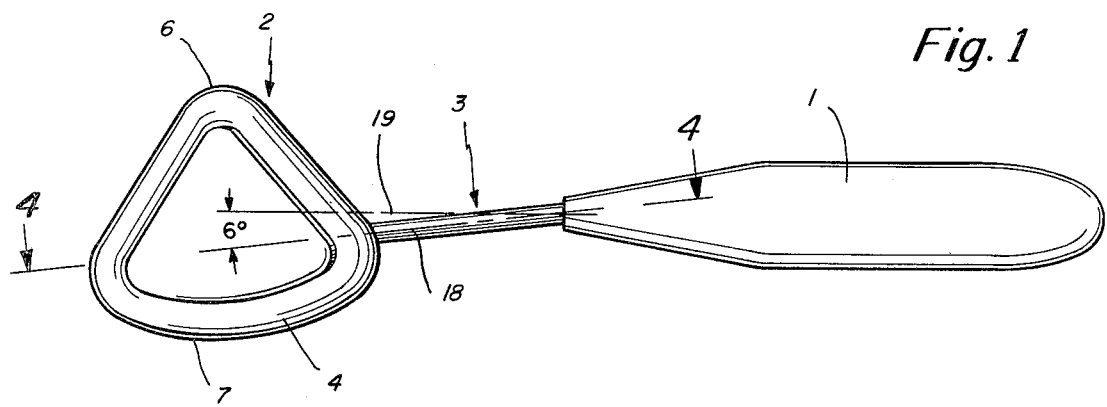
FIG. 1 is a plan view of a reflex hammer embodying the invention.
Figure 2:
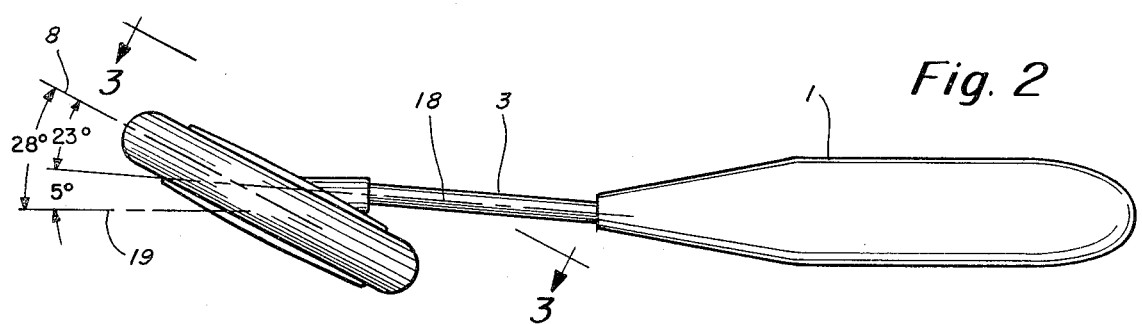
FIG. 2 is a plan elevation of the hammer shown in FIG. 1 looking upwardly from the lower edge of FIG. 1.
Figure 3:
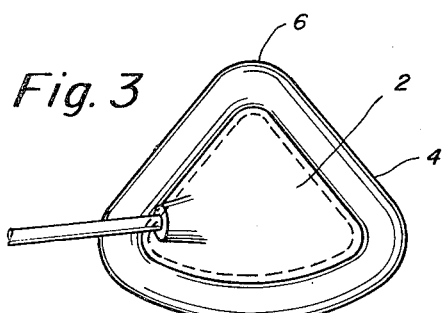
FIG. 3 is a fragmentary detail of the head of the hammer shown in FIG. 2 looking from the upper surface thereof.
Figure 4:
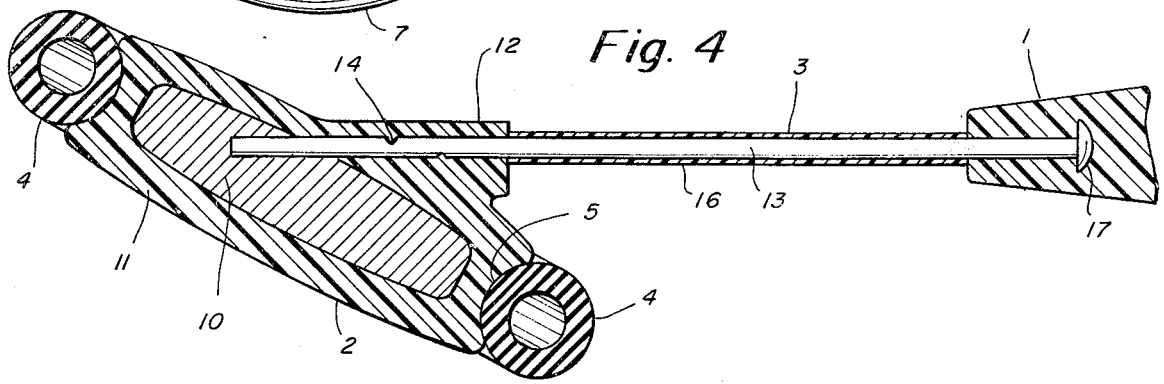
FIG. 4 is a cross sectional view taken substantially along the line 4—4 of FIG. 1.

Referring to the invention in the embodiment of FIG. 1, the handle 1 is connected to the head 2 by a flexible shaft 3. The head 2 has a somewhat flattened triangular shape as best illustrated in FIGS. 1 and 2. The periphery or rim of this flattened shape of the head is defined by a tubular or hollow compressible resilient rubber-like or rubber annular member 4. As illustrated in FIG. 4, this annular member 4 sits in a channel or groove 5 formed in the periphery or edge of the head 2. The rim formed by the tubular member 4 defines a corner or point 6 on one side of the head 2 and an elongated striking edge 7 on the other side of the head 2. The point 6 is rounded slightly, as illustrated, while the edge 7 has a slight arcuate configuration, also as illustrated in FIGS. 1 and 3. The point 6 and edge 7 lie in a common plane 8 that passes symmetrically through the major portion of the head as illustrated in FIG. 2. The head is weighted to form a heavy mass. It may be weighted in one of several forms. In a preferred form, the head is molded of a suitable plastic material with lead shot uniformly dispersed throughout. In another preferred embodiment, the head may be formed of a lead weight 10 with the outer portion of the head molded about the weight 10 and formed by the shell 11. The shell 11 is also integrally formed with a shaft receiving portion 12. This shaft receiving portion 12 connects the head to the flexible shaft 3. In a preferred embodiment, the flexible shaft 3 comprises an inner metal flexible rod 13 that extends into the head 2 and is securely embedded in the head. If desired and depending upon manufacturing techniques, the shaft 13 may extend into the lead weight 10 as illustrated in FIG. 4. The rod 13 may be provided with notches or other suitable means along its length in the head portion as illustrated at 14 so that molded plastic in the shell 11 may grip the rod 13 more effectively. For cosmetic purposes, the flexible rod 13 may be coated with a plastic sleeve 16 between the head 2 and handle 1.

The other end of the flexible rod 13 is molded into and permanently secured in the handle 1. The flexible rod 13 may be provided with a head 17 to assure that the rod will be permanently secured to the handle 1.

As illustrated in FIG. 2, the major plane 8 which is symmetrical with the head 2 lies at an acute angle to the axis 18 of the shaft. Preferably, this angle is an angle of 23°. The shaft 18 in turn lies at an angle of preferably 6° to the axis 19 of the handle 1. As viewed in FIG. 1, which is at 90° to the side view illustrated in FIG. 2, the axis 18 of the shaft is at an acute angle of 6° to the axis 19 of the handle. These angles of relation between the plane passing through the major portion of the head and the axis of the shaft and handle are p preferable. The angles provide an easier means of proper application for the hammer head to most reflex sites while at the same time permitting easy vision of the site while the hammer is being applied.

Figure 5:
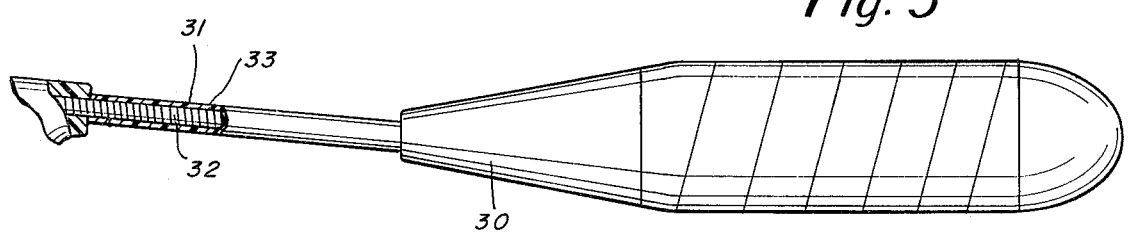
FIG. 5 is a fragmentary view of a flexible shaft and handle construction in an alternate embodiment.

In a modification of the invention as illustrated in FIG. 5, the handle 30 is suitably secured to a head by the flexible shaft 31 in a manner similar to that previously described. The flexible shaft in the embodiment of FIG. 5 preferably comprises a tightly wound helical spring 32 which is suitably embedded at its ends in the head and handle. The flexible helical spring 32 is covered with a plastic sleeve 33 which may if desired be integrally molded with the head and/or handle. The sleeve 32 is also flexible and permits movement of the helical metal spring 32.

Figure 6:
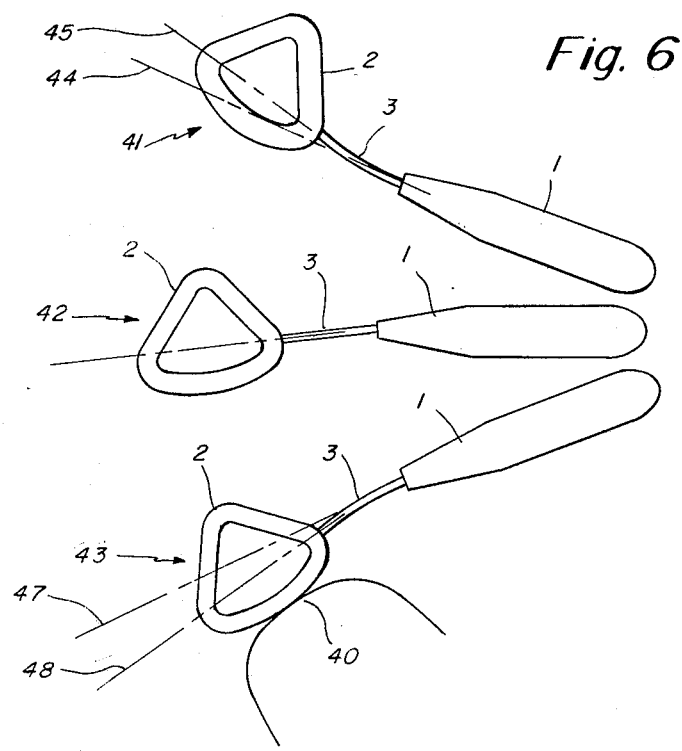
FIG. 6 are schematic views of a reflex hammer embodying the present invention in actual usage when striking the knee of an individual.

The application of the hammer is illustrated in FIG. 6 where its movement relative to a reflex site such as a knee 40 is shown. In this configuration, three positions of the hammer as it is moved to an impact position are illustrated without the hand of the person applying the hammer being shown. In the position illustrated in FIG. 6 at 41, the hammer has just begun its movement towards the knee 40. At the position illustrated at 42, the hammer has reached its half-way point and the position of impact is shown at 43, in an ideal application of the hammer. Because of the inertia of the mass of head 2 as the swing commences, as shown at 41, head 2 does not accelerate as fast as the shaft and handle. This is illustrated by lines 44 and 45. Line 44 represents an extension of the axis of the shaft 3 in its normal position while line 45 represents the actual position of this line at a moment shortly after the hammer begins its forward movement. As viewed in position 41, an initial force applied to the handle 1 is transmitted to the head 2 through the flexible shaft 3. This force accelerates the head 2 over an arcuate path towards the knee 40 at a rate slower than the rate of acceleration of the handle because the head 2 has a greater mass than the shaft 3 and because the shaft 3 is flexible. As the handle moves approximately half way towards the knee 40 to a position as illustrated at 42, the force applied to the head 2 is essentially increased because of the force stored in the spring-like flexible shaft 3. This causes greater relative acceleration of the head 2 so that by the time the hammer reaches approximately its mid point, the head 2 has assumed a position normal with respect to the handle 1. However, at the moment of impact illustrated at 43, the head 2 has accelerated at a rate faster than the movement of the handle 1 due to the increased forces applied to it. This causes the head 2 to essentially lead the handle 1 and shaft 3 and impact the knee 40 sooner than would occur had the shaft 3 been rigid. Line 47 illustrates the normal axis of shaft 3 while line 48 illustrates the projected axis of the upper portion of the shaft 3 at the moment of impact. Because the head 2 impacts the knee sooner, the moment of impact is faster than would otherwise occur if the shaft 3 were rigid. In addition, the resilience of the shaft 3 and its flexibility causes the head 2 to bounce off the reflex area faster, thus minimizing the damping effect that the head 2 would have if the handle were rigid and the head impacted the knee under such conditions. Having now described my invention,

I claim:

1. A hammer for testing neurological reflexes comprising a head, a flexible shaft and an elongated handle wherein a first and a second end of said flexible shaft is connected to said head and elongated handle, respectively, said head having an elongated striking edge extending and fixed at a first acute angle to said flexible shaft and said handle extending and fixed at a second acute angle to said flexible shaft.

2. A hammer as set forth in claim 1 having a plane passing through said edge and a major portion of said head with said plane passing through the axis of said flexible shaft at an acute angle.

3. A hammer as set forth in claim 2 wherein said head has a point lying in said plane.

4. A hammer as set forth in claim 3 having an annular compressible resilient member forming a peripheral rim positioned on said head and lying in said plane.

5. A hammer as set forth in claim 4 wherein said rim is formed of a tubular member.

6. A hammer as set forth in claims 1, 2, 3, 4 or 5 wherein said head has a mass greater than the mass of said shaft.

7. In a hammer for testing neurological reflexes having a handle connected to a head; the improvement comprising said handle including a flexible shaft connected at one end to said head and at the other end to a hand gripping portion of said handle so that said flexible shaft forms a first acute angle with said head and a second acute angle with said hand gripping portion of said handle.

8. A hammer as set forth in claim 1 wherein said head has a rim lying in a plane that is non-perpendicular to the axis of said shaft.

9. A hammer as set forth in claim 3 wherein said head comprises a central mass within said rim with said shaft connected at said one end to said central mass.

10. A hammer as set forth in claim 3 wherein said rim has a corner portion and an arcuate portion and said one end of said shaft intermediate said portions.

11. A hammer as set forth in claim 3 wherein the angle between said plane and said axis is in the order of 23°.

12. A hammer as set forth in claim 5 wherein said hand gripping portion is nonflexible.

13. In a neurological reflex testing hammer having a head constructed to impact a body part, a flexible, resilient shaft and an elongated handle wherein a first and second end of said flexible, resilient shaft is connected to said head and elongated handle, respectively, said head having a resilient elongated striking edge extending and fixed at an angle to said flexible shaft, said shaft formed and shaped with sufficient flexibility to cause said shaft to bend to an acute angle from its resting longitudinal axis when said handle is rapidly accelerated in an arcuate path, the improvement wherein said head has substantial mass and said shaft is sufficiently resilient so that when said hammer is swung and stopped before impacting said body part, the inertia of said head causes it to continue moving and flex said shaft, to strike said body part with said resilient striking edge and rebound without damping effects on the reflex movement.

14. A hammer as set forth in claim 13 having a plane passing through said edge and a major portion of said head with said plane passing through the axis of said flexible, resilient shaft at an acute angle.

15. A hammer as set forth in claim 14 having an annular compressible resilient tubular member forming a peripheral rim positioned on said head and lying in said plane.

16. A hammer as set forth in claims 13, 14 or 15 wherein said head has a mass greater than the mass of said shaft.

* * * * *